United States Patent [19]

Harrison

[11] Patent Number: 4,645,659
[45] Date of Patent: Feb. 24, 1987

[54] REAGENT FOR MAKING TECHNETIUM-99M LABELLED TIN COLLOID FOR BODY SCANNING

[75] Inventor: Roger C. Harrison, Amersham, England

[73] Assignee: Amersham International plc, Buckinghamshire, England

[21] Appl. No.: 599,828

[22] Filed: Apr. 13, 1984

[30] Foreign Application Priority Data

Apr. 13, 1983 [GB] United Kingdom ............... 8310038

[51] Int. Cl.$^4$ ...................... A61K 49/00; A61K 43/00
[52] U.S. Cl. .......................................... 424/1.1; 424/9; 422/61
[58] Field of Search ....................... 424/1.1, 9; 422/61

[56] References Cited

U.S. PATENT DOCUMENTS

| | | | |
|---|---|---|---|
| 3,992,513 | 11/1976 | Petkau et al. | 424/1.1 |
| 4,054,645 | 10/1977 | Hill et al. | 424/1.1 |
| 4,066,742 | 1/1978 | Garrett | 424/1.1 |
| 4,087,516 | 5/1978 | Laidler et al. | 424/1.1 |
| 4,094,965 | 6/1978 | Layne et al. | 424/1.1 |
| 4,107,283 | 8/1978 | Pratt et al. | 424/1.1 |
| 4,329,332 | 5/1982 | Couvreur et al. | 424/1.1 |
| 4,337,240 | 6/1982 | Saklad | 424/1.1 |
| 4,489,055 | 12/1984 | Couvreur et al. | 424/1.1 |

Primary Examiner—Christine M. Nucker
Attorney, Agent, or Firm—Wenderoth, Lind & Ponack

[57] ABSTRACT

A packaged reagent for making Technetium-99m labelled tin colloids comprises 0.75 to 750 μg stannous tin, 50 to 7000 μg sodium, potassium or ammonium ion, 40 to 5000 μg fluoride ion, 50 to 10,000 μg of a non-toxic non-ionic surface-active agent based on poly (alkylene oxide)glycol and a container aseptically enclosing said reagent. The presence of the surface-active agent, preferably one of the Pluronic types, results in smaller sized particles being produced on addition of pertechnetate to the reagent. This results in a higher liver/spleen biodistribution ratio.

14 Claims, No Drawings

REAGENT FOR MAKING TECHNETIUM-99M LABELLED TIN COLLOID FOR BODY SCANNING

British Patent Specification 1535847 describes a Technetium-99m labelled tin colloid for body scanning, particularly liver scanning. In the preparation of this colloid, an aqueous solution of a stannous salt is mixed with an excess of sodium, potassium or ammonium fluoride and the mixed solution freeze-dried. It is believed that there is formed a fluoro-stannite complex which is stabilised by excess fluoride. When the freeze-dried mixture is reconstituted by the addition of water or isotonic saline containing pertechetate ion, the complex is hydrolysed and there occurs simultaneous reduction and co-precipitation of the technetium with the colloidal tin hydrate.

By this method, the tin colloid is formed only at the time of labelling, so the labelled colloid can be stored only for a maximum of eight hours. This is an advantage over pre-formed tin colloids which may have to be stored for months but which are prone to deterioration. A liver scanning kit based on the invention of British 1535847 has been marketed and has achieved widespread commercial success. Uniform dispersion of the colloid particles in the aqueous medium has been achieved without the need to include a wetting agent or to take any other precautions.

However, this commercial kit does suffer from some disadvantages. The particle size is typically 1 to 3 microns, and might usefully be rather smaller. Occasionally, oversize particles are taken up in the lungs. Uptake by the spleen is higher than desired. The biodistribution of the colloid depends on the time between reconstitution and injection, and is somewhat less good after storage for 6 hours.

It is an object of the present invention to overcome these disadvantages, but without at the same time increasing the blood retention or reducing hepatic uptake of the colloid. This object is achieved by the use of a surface-active agent based on poly(alkylene oxide) gylcol and typified by those sold under the Trade Mark Pluronic.

The use of Pluronic F-68 in Technetium-99m labelled body scanning agents is not new. British Patent Specification 1343154 described a lung-scanning agent made by labelling pre-formed micro-particles with Technetium-99m, and uses Pluronic F-68 as a wetting agent to help suspending the particles. As is well-known, particles smaller than 5 to 8 microns to not become located in the lungs, so particles for lung scanning have a size range typically of 8 to 60 microns. It is natural that such pre-formed particles might need a wetting agent to prevent aggregation during storage and to assist suspension at the time of use.

The present invention provides in one aspect a method of making a Technetium 99m labelled tin colloid, which method comprises adding an aqueous solution of pertechnetate ion to a reagent comprising one part by weight of sodium, potassium or ammonium fluoride, from 0.00075 to 0.75 parts by weight of stannous ion and from 0.05 to 10, preferably from 0.1 to 5.0, parts by weight of a non-toxic non-ionic surface-active agent based on poly(alkylene oxide)glycol.

The reagent may be in aqueous solution but is preferably used as a freeze-dried solid. Suitably the solution of pertechnetate may be in water or in saline such as may conveniently be obtained by elution of a Technetium-99m generator; when the eluate is sterile, it is desirable that the reagent to which it is added should also be in a sterile state. There will normally be a large stoichiometric excess of stannous and fluoride ions over pertechnetate. The absolute amount of reagent used is governed by two parameters at different ends of the scale of use, i.e. at the lower end of the scale there must be sufficient reagent to reduce the Technetium-99m, whilst at the upper end of the scale toxicity of fluoride could become a limiting factor. Conveniently, from 2 to 200 mCi of Technetium-99m may be added to an amount of the above reagent containing 1 mg. of sodium, potassium or ammonium fluoride.

In another aspect, the present invention provides a packaged reagent for making Technetium-99m labelled tin colloids comprising:

Stannous tin, from 0.75 to 750 micrograms. sodium, potassium or ammonium ion, from 50 to 7,000 micrograms, flouride, from 40 to 5,000 micrograms a non-toxic non-ionic surface-active agent based on poly(alkylene oxide)glycol, from 50 to 10,000, preferably from 100 to 5,000, micrograms, and a container aseptically enclosing said reagent.

The reagent may be in aqueous solution, but is conveniently in freeze-dried form. The reagent may be prepared by providing in the container an aliquot of aqueous solution containing from 1 to 1,000 micrograms of stannous fluoride from 0.1 to 10 milligrams of sodium, potassium or ammonium fluoride and from 0.05 to 10, preferably 0.1 to 5.0, milligrams of the surface-active agent; freeze-drying the solution; sealing the container, preferably under a nitrogen atmosphere; the whole preparation being performed aseptically. Alternatively, terminal sterilization of the container and contents, e.g. by exposure to gamma radiation, may be performed.

The Pluronic series of surface-active agents are marketed in Europe by Pechiney Ugine Kuhlmann and manufactured by BASF/Wyandotte Chemicals. They are block copolymers having the general formula $$HO-(CH_2CH_2O)_a-(CH(CH_3)CH_2O)_b-(CH_2CH_2O)_c-H$$

where a and c are statistically equal. Variation of a, b, and c leads to a family of polymers, the molecular composition and physical form of the polyol being indicated by the number and prefix letter.

| Pluronic Surface-active agents | | |
|---|---|---|
| Pluronic No. | % $C_2H_4O$ | M.W. $(C_3H_6O)_b$ |
| L-31 | 10 | 950 |
| L-35 | 50 | 950 |
| F-38 | 80 | 950 |
| L-42 | 20 | 1200 |
| L-44 | 40 | 1200 |
| L-61 | 10 | 1750 |
| L-62 | 20 | 1750 |
| L-64 | 40 | 1750 |
| F-68 | 80 | 1750 |
| L-72 | 20 | 2050 |
| P-75 | 50 | 2050 |
| F-77 | 70 | 2050 |
| L-81 | 10 | 2250 |
| P-85 | 50 | 2250 |
| F-88 | 80 | 2250 |
| P-94 | 40 | 2750 |
| F-98 | 80 | 2750 |
| L-103 | 30 | 3250 |
| P-105 | 50 | 3250 |

| Pluronic Surface-active agents | | |
|---|---|---|
| Pluronic No. | % $C_2H_4O$ | M.W. $(C_3H_6O)_b$ |
| F-108 | 80 | 3250 |

The amount of surface-active agent used is not very critical as far as particle size reduction is concerned. Amounts of as little as 0.1 mg per vial are effective in reducing the particle size of the formed tin colloid by a substantial factor. However, the liver/spleen bio distribution ratio and the liver/background ratio are both critically dependent on the amount of surface-active agent, used. For instance, if too little surface-active agent is used, the liver/spleen biodistribution ratio is not stable whereas if too much is used, too much non-target activity is distributed around the body thus causing a reduction in the liver/background ratio. The use, in the present invention, of from 0.05 to 10 mg of surface-active agent therefore represents a convenient compromise between these two requirements. Preferably, however, the amount of surface-active agent is in the range of from 0.1 to 5.0 mg, particularly about 0.5 mg, per vial. In the present invention, liver/spleen biodistribution ratios can be selected by use of the appropriate surface-active agent quantity.

A variety of additives has been tried in place of surface-active agents based on poly(alkylene oxide)glycol but have been found not to give the same improvements. These include:

(a) Polyethylene glycol and polyvinyl acetate exhibited no major effect on particle size or stability.

(b) Gelatin, polyvinylpyrrolidone, hexadecyltrimethylammonium bromide and acacia satisfactorily reduced particle size but biodistribution in rats indicated that increased blood background resulted.

(c) Sodium lauryl sulphate gave rise to satisfactory particle size and blood background levels but reduced hepatic uptake.

EXAMPLES

In these examples, the test formulations were freeze-dried mixtures of 125 μg of stannous fluoride, 1.0 mg of sodium fluoride and the stated amount of Pluronic surface-active agent F38, F68 and F108. These vials were not sterilized by gamma-radiation but were manufactured aseptically. The mixture was reconstituted by the addition of 5-6 ml of pertechnetate eluate from a technetium generator in isotonic saline. The reconstitution of the solution was performed with gentle handling although, by employing the present invention, reconstituted solutions are generally less sensitive to rough handling than existing products. Unless otherwise stated, the reconstituted solutions was used immediately. The test animals in these examples were rats. The results are set out in Tables 1 to 4.

TABLE 1

Effect of Pluronic grade on particle size distribution

| Additive (per vial) | Particle size (microns) | | | | | | | |
|---|---|---|---|---|---|---|---|---|
| | >8 | 5-8 | 3-5 | 1-3 | 0.8-1 | 0.6-0.8 | 0.4-0.6 | <0.4 |
| None | 1.9 | 0.2 | 7.4 | 80.1 | 3.6 | 2.7 | | 3.0% |
| F38(2 mg) | 0.55 | 0.55 | (−0.15) | 2.65 | (−0.8) | (−1.25) | 2.5 | 96% |
| F68(2 mg) | 0.80 | (−0.2) | 0 | 1.50 | (−0.1) | 0.7 | 4.6 | 95.4% |
| F108(2 mg) | 0.70 | 0 | 0.15 | 1.10 | (−0.45) | 0.3 | 3.4 | 96.6% |

TABLE 2

Effect of Pluronic grade on animal biodistribution

| Additive | % Liver | % Spleen | % Lung | % Kidney | % Blood | % Carcass | Whole liver/ whole spleen | |
|---|---|---|---|---|---|---|---|---|
| None | 89.75 | 6.61 | 2.08 | 0.12 | 0.31 | 0.86 | 13.6 | 1 hour |
| | 85.29 | 7.37 | 3.96 | 0.35 | 0.66 | 2.06 | 11.6 | 6 hours |
| F38(2 mg) | 95.1 | 0.66 | 0.62 | 0.20 | 1.44 | 1.57 | 144 | 1 hour |
| | 96.24 | 0.78 | 0.84 | 0.13 | 0.60 | 1.06 | 123 | 6 hours |
| F68(2 mg) | 94.46 | 0.77 | 0.72 | 0.25 | 1.83 | 1.51 | 123 | 1 hour |
| | 96.28 | 1.06 | 0.49 | 0.14 | 0.65 | 0.97 | 91 | 6 hours |
| F108(2 mg) | 92.36 | 0.89 | 1.69 | 0.31 | 2.24 | 1.91 | 104 | 1 hour |
| | | | | | | | | 6 hours |

TABLE 3

Effect of Pluronic weight on particle size distribution

| Additive (mg/vial) F68 | Particle size (microns) | | | | | | |
|---|---|---|---|---|---|---|---|
| | >.5 | 1.0-5.0 | 0.6-1.0 | 0.4-0.6 | 0.1-0.4 | 0.05-0.1 | <0.05 |
| None | 4.2 | 81.3 | 11.5 | 1.4 | 0.3 | 1.3* | — |
| 0.1 | 4.4 | 23.6 | 10.2 | 47.0 | 11.8 | 3.0* | |
| 0.5 | 3.6 | 2.9 | 0 | 2.1 | 45.8 | 32.2 | 13.4 |
| 1.5 | 1.5 | 2.2 | 0.4 | 4.7 | 37.2 | 37.0 | 17.0 |
| 3.0 | 1.5 | 3.0 | 0.4 | 2.3 | 84.1 | 3.1 | 5.8 |

*<0.1 micron

TABLE 4

| Additive F68 (mg/Vial) | % Liver | % Spleen | % Lung | % Kidney | % Blood | % Carcass | Whole liver/ whole spleen | |
|---|---|---|---|---|---|---|---|---|
| None | 87.39 | 9.57 | 1.41 | 0.22 | 0.33 | 0.76 | 9.13 | 1 hour |
|  | 86.06 | 5.61 | 5.33 | 0.46 | 0.81 | 1.34 | 15.34 | 6 hours |
| 0.1 | 95.65 | 1.66 | 0.42 | 0.42 | 0.57 | 0.96 | 57.6 | 1 hour |
|  | 92.34 | 1.92 | 2.75 | 0.61 | 0.57 | 1.32 | 48.1 | 6 hours |
| 0.5 | 95.66 | 0.69 | 0.82 | 0.30 | 0.90 | 1.28 | 138.6 | initial |
|  | 95.59 | 1.53 | 0.75 | 0.22 | 0.38 | 1.22 | 62.48 | 7.5 hours |
| 1.5 | 94.35 | 0.85 | 0.70 | 0.44 | 1.24 | 1.89 | 111 | 1 hour |
|  | 95.41 | 0.80 | 0.35 | 0.30 | 0.67 | 1.85 | 119 | 6 hours |
| 30 | 95.0 | 2.22 | 0.42 | 0.17 | 0.90 | 0.90 | 42.8 | 1 hour |
|  | 95.32 | 2.26 | 0.38 | 0.18 | 0.61 | 0.95 | 42.2 | 6 hours |

Clinical trials are now being performed on humans. Satisfactory results have so far been obtained in these.

What is claimed is:

1. A packaged reagent for making Technetium-99m labelled tin colloids comprising:
    stannous tin, from 0.75 to 750 µg; sodium, potassium or ammonium ion, from 50 to 7,000 µg; fluoride, from 40 to 5,000 µg; a non-toxic non-ionic surface-active agent based on poly(alkylene oxide)-glycol, from 50 to 10,000 µg; and a container aseptically enclosing said reagent.

2. The packaged reagent as claimed in claim 1, wherein the reagent is a lyophilisate.

3. The packaged reagent as claimed in claim 1, wherein the non-toxic non-ionic surface-active agent comprises one or more non-toxic block copolymers having the formula $$HO-(CH_2CH_2O)_a-(CH(CH_3)CH_2O)_b-(CH_2CH_2O)_c-H$$

wherein a, b and c are integers and a and c are statistically equal.

4. A packaged reagent according to claim 3 wherein the block copolymer has a $C_2H_4O$ content of 80% and the M.W. of the group $(C_3H_6O)_b$ is 950, 1750 or 3250.

5. The packaged reagent as claimed in claim 1 wherein the surface-active agent is used in an amount of from 0.1 to 5.0 mg.

6. A method of making a Technetium-99m labelled tin colloid, which method comprises adding an aqueous solution of pertechnetate ion to a reagent comprising one part by weight of sodium, potassium or ammonium fluoride, from 0.00075 to 0.75 parts by weight of stannous ion and from 0.05 to 10 parts by weight of a non-toxic non-ionic surface-active agent based on poly(alkylene oxide)glycol.

7. The method as claimed in claim 6 wherein the reagent is a packaged reagent comprising:
    stannous tin, from 0.75 to 750 µg;
    sodium, potassium or ammonium ion, from 50 to 7,000 µg;
    fluoride, from 40 to 5,000 µg; a non-toxic, non-ionic surface-active agent based on poly(alkylene oxide)-glycol, from 50 to 10,000 µg;
    and a container aseptically enclosing said reagent.

8. The method as claimed in claim 6, wherein the reagent is a lyophilisate.

9. The method as claimed in claim 6, wherein the non-toxic non-ionic surface-active agent comprises one or more non-toxic block copolymers having the general formula $$HO-(CH_2CH_2O)_a-(CH(CH_3)CH_2O)_b-(CH_2CH_2O)_c-H$$

wherein, a, b and c are integers and a and c are statistically equal.

10. The method of claim 9 wherein the block copolymers has a $C_2H_4O$ content of 80% and the M.W. of the group $(C_3H_6O)_b$ is 950, 1750 or 3250.

11. The method as claimed in claim 7, wherein the surface-active agent is used in an amount of from 0.1 to 5.0 mg.

12. The method as claimed in claim 6, wherein the aqueous solution of pertechnetate is a solution in isotonic saline.

13. The method as claimed in claim 6, wherein the solution of pertechnetate and the reagent are both sterile.

14. The method as claimed in claim 6, wherein from 2 to 200 m Ci of Technetium-99m are used per 1 mg of sodium, potassium or ammonium fluoride in the reagent.

* * * * *